(12) United States Patent
Da Silva Ferraz et al.

(10) Patent No.: US 11,288,794 B2
(45) Date of Patent: Mar. 29, 2022

(54) DEVICE AND METHOD FOR BLOOD ANALYSIS BY IMAGE PROCESSING

(71) Applicant: UNIVERSIDADE DO MINHO, Braga (PT)

(72) Inventors: Ana Patricia Da Silva Ferraz, Arcozelo-Barcelos (PT); Vitor Hugo Mendes Da Costa Carvalho, Braga (PT)

(73) Assignee: UNIVERSIDADE DO MINHO, Braga (PT)

( * ) Notice: Subject to any disclaimer, the term of this patent is extended or adjusted under 35 U.S.C. 154(b) by 287 days.

(21) Appl. No.: 16/419,067

(22) Filed: May 22, 2019

(65) Prior Publication Data
US 2019/0272637 A1 Sep. 5, 2019

Related U.S. Application Data

(62) Division of application No. 14/783,347, filed as application No. PCT/IB2014/060531 on Apr. 8, 2014, now abandoned.

(30) Foreign Application Priority Data

Apr. 8, 2013 (PT) .......................................... 106871

(51) Int. Cl.
*G06T 7/00* (2017.01)
*G01N 15/00* (2006.01)
(Continued)

(52) U.S. Cl.
CPC ........... *G06T 7/0012* (2013.01); *G01N 15/00* (2013.01); *G01N 21/51* (2013.01); *G01N 33/86* (2013.01);
(Continued)

(58) Field of Classification Search
USPC .............. 422/72, 73, 415, 548; 436/8; 435/4
See application file for complete search history.

(56) References Cited

U.S. PATENT DOCUMENTS 4,687,638 A * 8/1987 Benajam ................ G01N 21/82
422/73
5,169,601 A 12/1992 Ohta et al.
(Continued)

FOREIGN PATENT DOCUMENTS

EP 1397679 B1 1/2010
EP 1797426 B1 1/2010

OTHER PUBLICATIONS

V. Moreira, et al; Design of a mechatronic system for human blood typing in emergency situations; Proceedings of 2012 IEEE; pp. 1-4.
(Continued)

*Primary Examiner* — Dean Kwak
(74) *Attorney, Agent, or Firm* — Lucas & Mercanti, LLP

(57) ABSTRACT

The present application describes a new device and method of use thereof, which allows identifying certain antigens and antibodies present in the blood. The device of the present invention is a closed device consisting of two parts, wherein the upper part has a chamber surrounded by LEDs illuminating the analysis plate, which is supported by the rotating platform. In turn, the rotating platform is connected to a motor that will promote the rotation thereof for mixing reagents with blood. After a period of time, the camera will capture and send the resulting image to a computer program that will analyze the sample, using image processing techniques.

6 Claims, 5 Drawing Sheets

(51) Int. Cl.
  *G01N 21/51* (2006.01)
  *G01N 33/86* (2006.01)
  *G06T 7/62* (2017.01)
  *G06T 7/13* (2017.01)
  *G06T 7/90* (2017.01)
  *G06T 7/70* (2017.01)
  *G06K 9/46* (2006.01)
  *G06K 9/52* (2006.01)
  *G06K 9/62* (2022.01)
  *G06T 5/00* (2006.01)
  *G01N 35/00* (2006.01)
  *G01N 35/04* (2006.01)

(52) U.S. Cl.
  CPC ......... *G06K 9/4604* (2013.01); *G06K 9/4652* (2013.01); *G06K 9/52* (2013.01); *G06K 9/6267* (2013.01); *G06T 5/00* (2013.01); *G06T 7/13* (2017.01); *G06T 7/62* (2017.01); *G06T 7/70* (2017.01); *G06T 7/90* (2017.01); *G01N 2015/0092* (2013.01); *G01N 2035/00524* (2013.01); *G01N 2035/0475* (2013.01); *G01N 2201/062* (2013.01); *G06K 2009/4666* (2013.01)

(56) References Cited

U.S. PATENT DOCUMENTS

| | | |
|---|---|---|
| 5,594,808 A | 1/1997 | Shen et al. |
| 5,620,898 A | 4/1997 | Yaremko et al. |
| 5,774,214 A | 6/1998 | Prettyjohns |
| 6,330,058 B1 | 12/2001 | Garcia-Rubio |
| 7,989,177 B2 | 8/2011 | Bystryak et al. |
| 8,053,226 B2 | 11/2011 | Schwind et al. |
| 8,057,377 B2 | 11/2011 | Holmes et al. |
| 8,318,439 B2 | 11/2012 | Battrell et al. |
| 2010/0221741 A1 | 9/2010 | Saiki et al. |

OTHER PUBLICATIONS

K. Bezerra, et al; Advanced design of a mechatronic system for human blood typing; The Romanian Review Precision Mechanics; Optics & Mechatronics; 2012; No. 41; pp. 144-150.

A. Ferraz; et al; Characterization of blood samples using image processing techniques; Sensors and Actuators A: Physical; vol. 172; 2011; pp. 308-314.

International Search Report dated Aug. 22, 2014 for Application No. PCT/IB2014/060531 and English translation.

\* cited by examiner

DEVICE AND METHOD FOR BLOOD ANALYSIS BY IMAGE PROCESSING

CROSS REFERENCE TO RELATED APPLICATION

This Application is divisional of U.S. application Ser. No. 14/783,347, filed Oct. 8, 2015, which is a 371 of PCT/IB2014/060531 filed on Apr. 8, 2014 which, in turn, claimed the priority of Portuguese Patent Application No. 106871 filed on Apr. 8, 2013, the contents of each of which are incorporated herein by reference.

TECHNICAL FIELD

The present invention relates to a device for detecting immunological agglutination. More specifically, it is a device that enables detection of the different blood groups, as well as certain blood diseases via agglutination of blood cells by image processing techniques.

BACKGROUND

Currently, blood grouping, in emergency situations, is a lengthy test in view of the immediate need for blood. In these situations, the current practice is to administer the blood type O negative, given the lower risk of incompatibility as it is considered the universal donor. However, although the risk is lower, there are still possible reactions which can be prevented by administering a blood type compatible with the patient's one, starting from the first unit of blood transfusion.

The present invention is in the field of determining some antigens and antibodies present in the patient's blood, using methods that are suited to emergency situations in order to speed up the determination.

Red blood cells have on their surface a variety of relevant antigens for blood transfusion. These antigens are grouped into systems such as ABO, D (Rh), Kell, Duffy, Kidd, Lewis, P, MNS, Lutheran, Kidd and Xg, being the ABO and D (Rh) systems the most relevant in the context of transfusions.

Decades ago, blood transfusion from one individual to another have shown the importance of transfusions and existing incompatibilities. The person transfused often got sick and occasionally died after transfusion. Accordingly, it was found that there were different antigens on the surface of red blood cells and antibodies in plasma and that blood transfusion in patients with different antigens resulted in blood agglutination due to the occurrence of antigen-antibody reaction. The ABO system is then described, and included types A, B, AB and O. Subjects with type A have in their red blood cells the antigen A, while their plasma contains anti-B antibodies. Individuals with type B have red blood cells with B antigens and in their plasma anti-A type antibodies. Individuals with type AB have both antigens of type A and type B and do not have antibodies in their plasma. Finally, the individuals of type O, or more correctly type zero (0), have not antigens on the red blood cells and have anti-A and anti-B antibodies in their plasma.

D (Rh) system is the second most importance in the context of blood transfusion, and it is usually described in conjunction with the ABO system with the "positive" or "negative" suffix, such as for example, AB positive, O negative. Its importance stems from its large ability for producing agglutination when administered to an incompatible type, such as for example, administering a positive Rh to a negative Rh individual.

In addition to these two most significant systems for blood transfusion, many others are present on the surface of red blood cells. There are some extremely rare antigens, while others can be found in the general population. The Kell system is among the least rare, followed by Duffy, Kidd, Lewis, P, MNS, Lutheran and Xg.

Tests for determining blood types are based on the agglutination reaction. In these tests, an individual's blood is mixed with specific reagents that, for example, identify the antigen present in the blood, such as reagents anti-A, anti-B, anti-AB and anti-D. Thus, red blood cells in the individual's blood will have certain antigens that in contact with each antibody-containing reagent will trigger antigen type-dependent reactions. In this study, each of the reactions taking place is observable by naked eye and through image processing.

To avoid problems during blood transfusion, a number of different solutions have been developed.

According to U.S. Pat. No. 6,330,058 patent, ABO and D (Rh) blood analysis is performed by a system developed using a spectrophotometric method.

U.S. Pat. No. 8,318,439 patent application discloses a system capable of performing blood type analyzes such as ABO and D (Rh) determinations, phenotypes, minor crossmatch, cross-matching, antibody screening and identification of some diseases such as malaria, typhoid fever. For this, it uses optical detection which could include transmittance and reflectance spectroscopy, turbidimetry—where light is measured at a 180 degrees angle from the incident—nephelometry—where light is measured at 90 degrees from the incident, or any other by an angle from the incident beam, including the front and back scattering—laser scattering spectroscopy, or visual observation. It has been found that this system, besides being different from the present inventions, is a more time consuming process and does not identify the antigens present in the blood of the individual. It has also been found that this system requires its use only in the laboratory, not suiting emergencies.

Patent document U.S. Pat. No. 8,053,226 discloses a system that performs phenotype and antibody identifications with lateral flow tests. Reading of the results is performed by naked eye or with a CCD camera. The difference between the new invention and this document is that it describes a lateral flow test while the new invention refers to a slide test.

Patent document EP 1397679, relates to a clinically intelligent diagnostic device for diagnosing diseases according to related symptoms but also for performing ABO and Rh blood analysis. Furthermore, it performs phenotype and disease identification tests such as HIV, and syphilis. This device uses microarrays and suits to the technologies currently used in laboratories. It has been found that the methodology and related technology are different from the new invention.

Patent document EP 1797426 shows a system that uses a quartz crystal microbalance detection-based technology (quartz crystal microbalance QCM). This technology is used for rapid monitoring of direct and indirect blood types, performing the hepatitis test as well. The system is totally different from what is intended to patent.

In turn, Moreira, V. et al, documents refer to a portable blood analysis device which incorporates therein a camera that captures the image which is reflected by a mirror which is—laterally positioned to the analysis plate. The analysis plate is in turn moved by a cam—placed vertically, coupled to a horizontal shaft of a rotary electrical motor—which by rotating, at constant speed, the respective profile causes the horizontal plate to oscillate in an up and down movement so mixing occurs. The system differs from the present invention as image acquisition is made using a mirror placed between the camera and the sample plate. This may lid to reading inaccuracies (acquired image distortion which is not compensated by the system), which may then lid to an analysis with possible failures. Furthermore, plate placement has to follow a mechanical guiding of the plate and part of the analysis plate is not covered in full and so the reactions for the analysis are not fully covered, resulting in a misleading and problematic analysis for the patient. Moreover, the invention described in these documents mentions that the selection of the area to be examined is performed manually.

The present invention relates to a new system that automates the reading and interpretation of results, which are a major source of errors in the administration of incompatible blood. The determination time is smaller as compared to the above identified documents, since it uses the slide test in conjunction with image processing techniques that do not increase the test time.

The slide test is the blood type determination test displaying results in a shorter time, with a very simple test procedure:
1. Label clean glass slides with convenient letters to identify the test to be carried out;
2. Pipette one drop of each reagent to the slides;
3. Next to each drop of reagent, add a drop of whole blood, having ¼ of the reagent drop size, or plasma depending on the test concerned;
4. Using a mixing rod, mix uniformly the reagent and the blood or plasma in a 2.5 $cm^2$ area;
5. Results are verified macroscopically to detect signs of agglutination, while rotating the slide.

In most cases, agglutination occurs within a few seconds, but not to ignore weaker antigens or antibodies, the results should only be interpreted after 2 minutes, such as indicated in the package insert of the procedure for the slide test.

Interpretation of results depends on the test type under analysis, but basically it is determined by combining the occurrence or non-occurrence of agglutination.

The occurrence of agglutination identifies the antigen or antibody under analysis, while the non-occurrence means that the antigen or antibody under study is not present in the blood analyzed. In the cross-matching, the occurrence of agglutination means that reaction will occur between the donor and the receiver and, therefore, such blood transfusion should not be performed.

Since results are currently analyzed by naked eye, that is, in a visual way, the possibility of misinterpretation of results may arise and, therefore, it is proposed the developed device, such that by capturing the results in an image form and a computer program developed for this purpose, the correct identification of agglutination is obtained.

Nevertheless, contemplation of new tests, such as minor cross-match, cross-matching, phenotypes, research and identification of antibodies, which are also necessary and essential for performing a blood transfusion, even in emergency situations, neither have been published, nor disclosed to the scientific community, and in spite of the several efforts to automate these techniques, as disclosed in the above-mentioned patents, these systems still have a longer time for results than those expected for the presented methodology.

This technology also provides for identifying some diseases, such as, Typhoid Fever, Brucella, Tick Fever, Syphilis, Mononucleosis, Hospital infections, Streptococcus bacteria, Meningitis and Pneumonia, which albeit being in some cases identified by other systems, the methodology and equipment are different and in the case of Brucella disease, Tick Fever, Mononucleosis, Meningitis and Pneumonia, no system was found allowing such a fast analysis.

Abstract

In the present application, a portable device for detecting the immunological agglutination of blood samples is described, which allows identifying certain antigens and antibodies in blood, characterized by comprising:
   an upper part (1) closed with a lid (2), comprising a camera (3) which is centered surrounded by LEDs (4) and connected to a laptop computer or other mobile device which analyzes the captured images by image processing techniques;
   a lower part (5), which in turn comprises a rotating platform (6) connected to a motor (7) where the analysis plate (8) is fixed;
   a power supply.

In a preferred embodiment, the device still has a connection to a laptop computer or other mobile device performed via USB, Wireless or Bluetooth, including a mobile phone (smartphone) or tablet.

In another preferred embodiment, the camera (3) of said device focuses directly on the rotating platform (6).

In yet another preferred embodiment, the upper part (1) and the lower part (5) of the device are connected by a hinge on one side and a lock on the opposite side.

In a preferred embodiment, the camera (3) focuses directly on the analysis plate (8).

In another preferred embodiment, the analysis plate (8) is sealed and transparent, and is a whole piece and comprises separate circular containers (9), which are made of a sealing and impermeable material and having holes (10).

In yet another preferred embodiment, the analysis plate (8) is sealed and transparent, having a removable lid (11) which fits on the base with the containers by a thread mechanism that joins and fixes the two parts (lid and base with containers) and seals the liquid outlet.

In a preferred embodiment, the analysis plate (8) used has 6 containers (9).

In another preferred embodiment, the analysis plate is also a spinning one (12) having circular and deep containers (13).

In a yet preferred embodiment, the number of LEDs (4) ranges between 4 and 6.

In a preferred embodiment, the power supply of the above described device is a battery.

In a preferred embodiment, the method for detecting immunological agglutination of blood samples, using the above described device comprises the following steps:
a) Place each of the reagents in their respective containers of the analysis plate, and then the patient's blood to be analyzed, both in their respective proportions;
b) Then, place the analysis plate (8) in the device, fixing it to the rotating platform (6);
c) Close the device by joining the upper part of the device (1) with the lower part (5) and start the device;
d) The device activates the camera (3), LEDs (4) and motor (7), according to the following steps:
   i. The motor (7) moves rotationally the platform (6) for a time between 60 and 130 seconds, during which the reaction takes place;
   ii. The motor (7) stops and the LEDs (4) are turned on;
   iii. After 2 minutes, the camera (3) captures the image;
e) LEDs (4) are turned off;
f) The camera's image is sent to the mobile device, which in turn stores this image;
g) The image is treated by image processing techniques;

h) The classification algorithm classifies the occurrence or non-occurrence of agglutination according to the standard deviation value obtained for each of the test containers.

In another preferred embodiment, the blood to reagents ratio consists of a drop of whole blood having one-forth of the reagent drop size.

In yet another preferred embodiment, the image processing techniques used comprise the following steps:
a) Extracting the green color planes of the captured image, by transforming the original 32-bit image into an 8-bit image so it can be used;
b) Separating the blood and reagent mixtures into two regions, designated particle region and background region, by assigning the value 1 (one) to all pixels belonging to a range of established values and assigning the value 0 (zero) to all other pixels in the image that does not belong to such established range;
c) Calculating the threshold value for each pixel based on statistics of the adjacent pixel, using a 32-width and 32-height default matrix (kernel), with a deviation factor which by default is 0.20;
d) In the image, assigning the value 1 (one) of pixel to existing holes in the particles corresponding to the blood and reagent mixtures;
e) Then, removing the particles with the value of 1 (one) pixel to remove background noise from the image and ensure that at the end only remain the particles related to the test containers;
f) Removing the particles which are on the borders of the image, filling in the position with the same value of the adjacent pixel in order to ensure that only remain for analyzing the particles related to the test containers;
g) Calculating the metrics on the CenterofMassX and CenterofMassY image, which together provide the coordinates of the center of mass of each particle in the image;
h) Extracting the light planes from the original image and transforming the image into an 8-bit image, which can now be used by other functions;
i) Referencing the object in the image that is an identifying mark of the order in which the test was performed, keeping a profile of such object and searching for such object in each of the images analyzed by the program, giving the coordinates and calculating distances to other objects;
j) Identifying in each image six containers and presenting of the coordinates of each one in order to calculate the aforementioned distances;
k) Quantifying a given image region defined by the programmer, using each of the container's coordinates given in the previous function to quantify a set of metrics as average of pixels, minimum value, maximum value, standard deviation and analyzed area, because the standard deviation values determines whether or not agglutination has occurred in each test container.

In a preferred embodiment, if the standard deviation is higher than 16, the classification algorithm classifies as agglutinated.

In another preferred embodiment, if the standard deviation is less than 16, the classification algorithm classifies as not agglutinated.

In another preferred embodiment, the results are sent by SMS or email.

In a preferred embodiment, the blood type detection by determining ABO and Rh; Tick Fever, Syphilis, Mononucleosis, Hospital infections, Streptococcus bacteria, Meningitis and Pneumonia.

General Description

The present invention is a new device and a method of use thereof which allows identifying certain antigens and antibodies present in the blood.

As is known to anyone skilled in the field of blood transfusion, before administering a blood transfusion, it is essential to perform some pre-transfusion testing, such as for example, ABO and D (Rh) determination; ABO minor cross-matching; Rh (C, c, E and e) and Kell (K) phenotyping; complete phenotyping (Duffy, Kidd, Lewis, P, MNS, Lutheran, Kidd and Xg); antibody research; antibody identification (for positive antibody research results) and cross-matching. These tests are crucial for avoiding any transfusion-derived problem.

Having as an object the development of a system enabling fast results from the above mentioned tests and obtaining results for the testing of typhoid fever, brucela, tick fever, syphilis, mononucleosis, hospital infections, streptococcus bacteria, meningitis and pneumonia as well, a new device using slide methodology has been developed. These diseases can be detected in this new device and methodology, resorting also to existing tests for each disease, including: Widal test; Wright test; Weil-Felix test (tick fever); VDRL (syphilis); Mononucleosis; MRSA and MSSA SLIDEX (hospital infections); Stepto Plus SLIDEX (streptococcus bacteria); SLIDEX Meningitis-Kit5 (meningitis) and SLIDEX pneumo-Kit (Pneumonia).

As compared to existing documents and systems, this methodology will reduce the time for results for each of these tests, enabling its suitability for emergency situations where time is a factor of paramount importance; it will also enable the physical down-sizing of the ultimate system do be developed.

It also enables fast tests for some diseases which are not included in the current systems. Furthermore, the fact that the application has been developed for different operating systems, it will enable its use by a wider range of devices, assisting to the worldwide suitability of this methodology, either in an underdeveloped or developed region. Thus, it is intended to have in a few minutes a complete profile of the individual's blood type and blood compatibilities, as well as the study of some diseases that might be useful depending on the clinical scenario.

The developed system is limited in size to be portable and inexpensive. Thus, this system has been developed with two approaches, one incorporating a laptop, such as a tablet or mini-pc, and another having a mobile phone (smartphone) operating-based possibility, which together with a developed application will perform the full test analysis and results achievement. This application can be used with the system, which will perform automatically all the tests or can also be used without the system, where, for example, underdeveloped countries could purchase the application and, even when performing the test manually, would always have a non-subjective outcome, devoid of human interpretation error.

Device

The device of the present invention is a portable device consisting of two parts, the upper part (1) closed by a lid (2) and the lower part (5). The upper part (1) comprises a digital camera (3) which is fixed in the center of the upper part, directly focusing on the region of the sample to be analyzed, surrounded by lighting, which may have between 4 and 6 LEDs (4) for a good image view and, consequently, whether or not agglutination has occurred. The LEDs will illuminate the analysis plate (8) located in the lower part of the device (5), more specifically the rotating platform (6). The lower part of the device (5) comprises a motor (7), which is connected to the rotating platform (6) where the plate having a test sample (8) is securely fitted.

The rotating platform (6) securely fits the closed analysis plate (8) containing six separate containers, consisting of sealing and impermeable material and having a hole (10).

The camera is connected to a laptop computer or another mobile device such as a phone (smartphone) or a tablet via USB, Wireless or Bluetooth, which analyzes the captured images through image processing techniques.

The incorporation of a camera connected to the Internet via USB, Wireless or Bluetooth enables sending the captured image to the equipment referred in the previous paragraph. Through an application developed for different operating systems, the image can be used in any such equipment.

Methods of Analysis

The method for detecting immunological agglutination of blood samples uses the above described device and comprises the following steps:

a) Place each of the reagents in their respective containers of the analysis plate (8), and then the patient's blood to be analyzed, both in their respective proportions, i.e. 50 µL of each reagent and 1 small drop of whole blood having ¼ of reagent drop size;
b) Then, place the analysis plate (8) in the device, fixing it to the rotating platform (6), in order to avoid any displacement possibility during processing due to the high motor (7) speeds.
c) Close the device by joining the upper part of the device (1) with the lower part (5) and start the device;
d) The device activates the camera (3), LEDs (4) and motor (7), according to the following steps:
  i. The motor (7) moves rotationally the platform (6) for a time between 60 and 130 seconds, during which the reaction takes place;
  ii. The motor (7) stops and the LEDs (4) are turned on;
  iii. The camera (3) captures the image after 2 minutes only, so that weaker reactions are not hidden;
e) LEDs (4) are turned off;
f) The camera's image is sent to the mobile device, which in turn stores this image;
g) The image is treated by image processing techniques;
h) The classification algorithm classifies the occurrence or non-occurrence of agglutination according to the standard deviation value obtained for each of the test containers.

Image Processing Techniques

The image processing techniques used in the blood analysis method through the above described device comprise the following steps:

a) Extract the green color planes of the captured image by transforming the original 32-bit image into an 8-bit image so it can be used;
b) Separate the blood and reagent mixtures into two regions, designated particle region and background region, by assigning the value 1 (one) to all pixels belonging to a range of established values and assigning the value 0 (zero) to all other pixels in the image that does not belong to such established range;
c) Calculate the threshold value for each pixel based on statistics of the adjacent pixel, using a 32-width and 32-height default matrix (kernel), with a deviation factor which by default is 0.20;
d) In the image, assign the value 1 (one) to existing holes in the particles corresponding to the blood and reagent mixtures;
e) Then, remove the particles with the value 1 (one) to remove background noise from the image and ensure that at the end only remain the particles related to the test containers;
f) Remove the particles which are on the borders of the image, filling in the position with the same value of the adjacent pixel, in order to ensure that only remain for analyzing the particles related to test containers;
g) Calculate the metrics on the CenterofMassX and CenterofMassY image, which together provide the coordinates of the center of mass of each particle in the image;
h) Extract the light planes from the original image and transform the image into an 8-bit image, which can now be used by other functions;
i) Reference the object in the image that is an identifying mark of the order in which the test was performed, keeping a profile of such object and searching for such object in each image analyzed by the program, giving the coordinates and calculating the distances to other objects;
j) Identify in each image six containers and present the coordinates of each in order to calculate the aforementioned distances;
k) Quantify a given image region defined by the programmer, using each of the container's coordinates given in the previous function to quantify a set of metrics as average of pixels, minimum value, maximum value, standard deviation and analyzed area, because the standard deviation value determines whether or not agglutination has occurred in each test container;

Classification Algorithm and Results

If the calculated standard deviation is less than 16, the classification algorithm classifies as not agglutinated.

On the other hand, if the calculated standard deviation is greater than 16, the classification algorithm classifies as agglutinated.

System Advantages

The major advantages of this system are based on the following features:
  uses the slide test which is a fast test as regards to results achievement and that perfectly fits to emergency situations;
  mixing is fully automatically performed, having neither user intervention nor related human errors;
  there are no contaminations between samples, given the analysis plate and containers construction;
  whole process of reading and interpretation of results is also automated and optimized, which again reduces human errors associated with the test procedure.

Thus, entire procedure takes approximately 3 minutes and the results are reliable and accurate, with no associated human errors. Furthermore, due to its construction, the device has a small size, fitting perfectly to emergency situations.

BRIEF DESCRIPTION OF THE FIGURES

For an easier understanding of the invention, figures representing preferred embodiments of the invention area appended which, however, do not intend to limit the subject matter of this application.

DESCRIPTION OF EMBODIMENTS

Device

Figure 1:
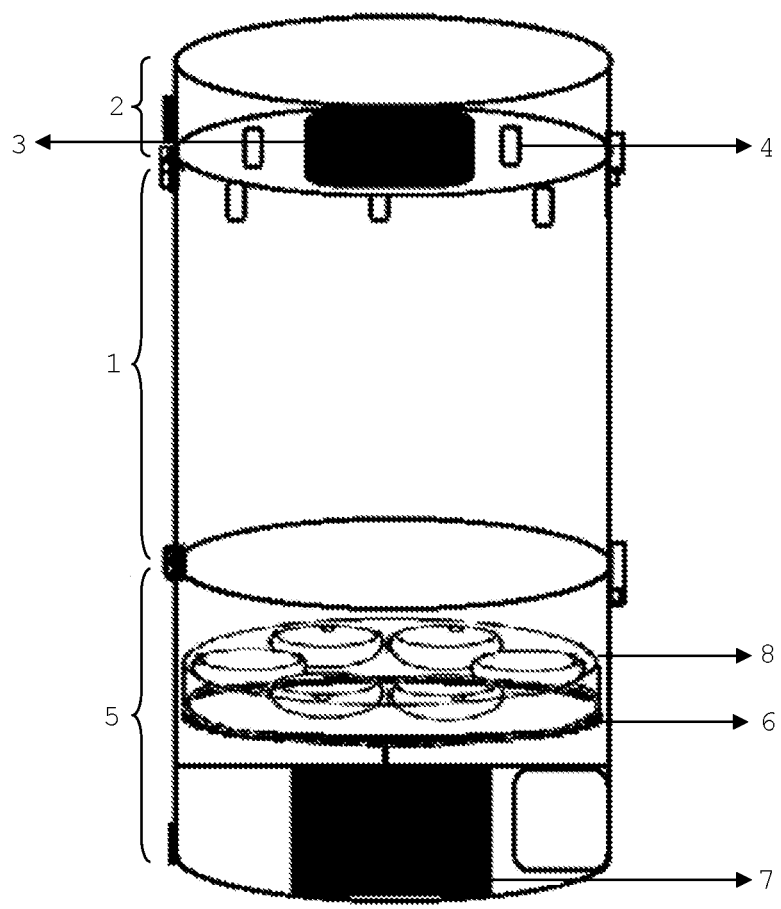
FIG. 1 illustrates a representation of the device wherein (5) is the lower part, (1) the upper part; (3) the camera; (4) the LEDs; (8) the analysis plate; (6) the rotating platform; (7) the motor and (2) the lid.
Figure 2:
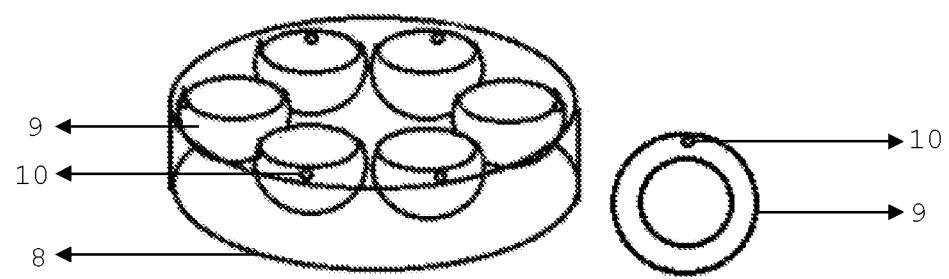
FIG. 2 illustrates a representation of the analysis plate (8).
Figure 3:
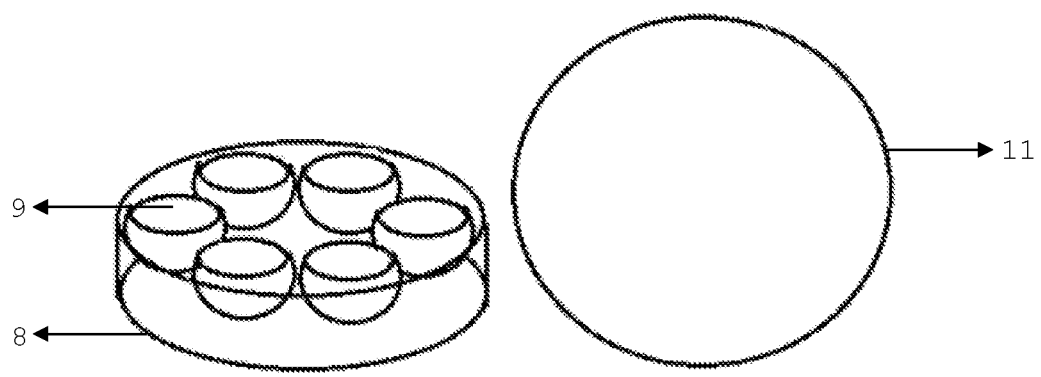
FIG. 3 illustrates a representation of the analysis plate (8) and the respective lid (11).
Figure 4:
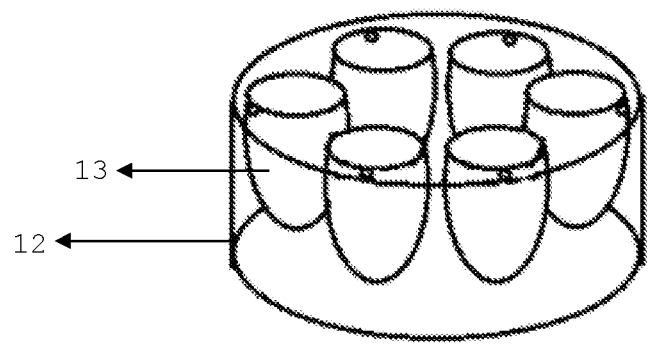
FIG. 4 illustrates a representation of the spinning plate (12) with the respective containers (13).
Figure 5:
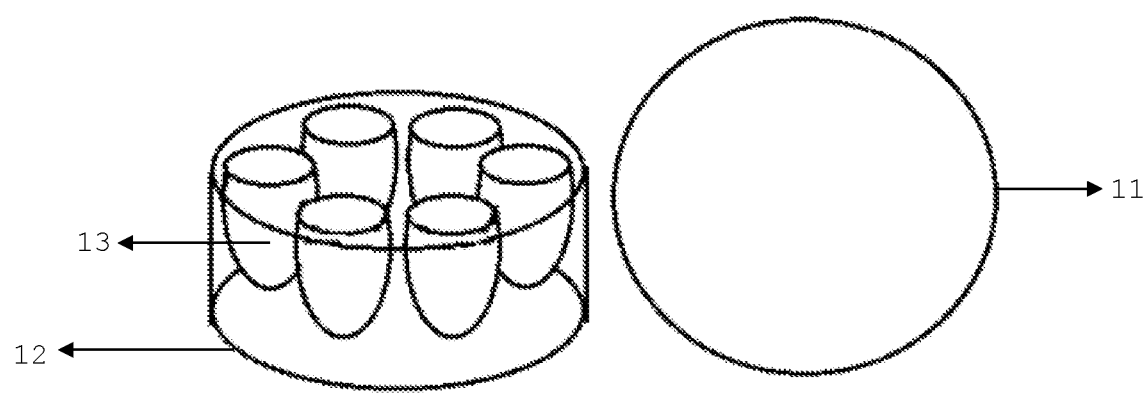
FIG. 5 illustrates a representation of a spinning plate with a lid (11).

The device of the present invention is a portable device consisting of two parts, the upper (1) and lower (5). The upper part (1) comprises a digital camera (3) which is fixed in the center of the upper part, directly focusing on the region of the sample to be analyzed, surrounded by lighting, which may have between 4 and 6 LEDs (4) for a good image view and, consequently, whether or not agglutination has occurred. The LEDs will illuminate the analysis plate (8) located in the lower part of the device (5), more specifically in the rotating platform (6). The lower part of the device (5) comprises a motor (7) which is connected to the rotating platform (6) where the respective plate having a test sample (8) is securely fitted. The plate may be of tests (8) or spinning (12), i.e. containers are deeper.

The camera is connected to a laptop computer or another mobile device such as a phone (smartphone) or tablet via USB, Wireless or Bluetooth, which analyzes the captured images through image processing techniques.

The incorporation of a camera connected to the internet via USB, Wireless or Bluetooth enables sending the captured image to the equipment referred in the previous paragraph. Through an application developed for different operating systems, the image can be used in any such equipment.

The device is closed, due to the existence of a lid (2), with no ambient light input, which prevents the existence or interference of artifacts in the image, which could compromise the entire analysis performed, providing a wrong blood type result.

The fact that the camera focus directly on the samples enables capture of a whole image and therefore a complete analysis of all reactions.

The rotating platform (6) securely fits the respective closed analysis plate (8) having six separate containers, which have holes made of a sealable and impermeable material (10).

The upper part (1) and the lower part (5) of the device may be connected by a hinge on one side and a lock on the opposite side.

Motor can reach speeds between 0 and 13446 rpm.

The mixing and motor starting is made through a switch and there is a potentiometer for regulating the motor speed, depending on whether an analysis or spinning is performed, and a timer for controlling the run time of each test.

The rotating platform is the basic part of the system which assists in promoting the mixing of the components that are on the board, since it is directly connected to the motor. This basic part has a simple fitting system to allow entry and exit of the test and spinning plates.

The camera and LEDs are properly protected by a fitting that allows easy access to both for future repairs and replacement of LEDs, if necessary.

Importantly, both system and camera require a power supply, which is easily provided by a battery.

The plates have two possibilities for introducing liquids:
one in which the plate is a whole with a fixed lid and has in each container a small hole sealed by an impermeable material, allowing only the passage of a needle for introducing blood and reagent, and preventing discharge of blood even during the mixing process where the speeds are high;
one in which the plate is dismountable and has a removable lid that allows the introduction of blood and reagent and may be fitted again by means of a thread, being the parts fixed by rotating the lid on the plate, in such a way that there is neither a leakage of blood and reagent, nor mixing between containers.

In the latter plate, the sealing mechanism is a thread that allows joining both parts (lid and base with containers) completely sealing liquid spillage.

Both plates are properly sealed for having no contamination or mixing between blood and reagent containers and are transparent for easily capturing the image.

Containers are separate and sealed (isolated), enabling no contamination between samples—in the claimed device the blood will be introduced through the small holes present in each container only, not being necessary to open the analysis plate;

Given the speed that the motor can reach, if blood spinning is required, it can be performed on the device, in order to obtain plasma segregated from its components, which might be used to perform some tests. For this, a spinning plate (12) is used in which containers must be deeper (13) for accommodating a larger amount of blood (total liquid) than the plate used in tests.

The container walls are circular, such that, in the event of blood and reagents deposition, these will always have the tendency to drain/go down to the bottom of the container and deposit/accumulate there. Thus, the liquid will always be deposited at the base of the container and with a good area with the reaction to analyze.

The base of containers can be not completely round. The base of the container is flat or planar to facilitate visualization of the reactions between blood and reagent. Thus, although the plate is currently in the format shown, having some concavity, the same plate completely straight might be used with flat-based containers.

According to the methodology of the slide test, a drop of blood having ¼ of the reagent drop size or plasma should be inserted, depending on the test concerned.

Method of Analysis

The method of analysis of the blood sample comprises the following steps:
a) Place each of the reagents in their respective containers (9) of the analysis plate (8), and then the blood to be analyzed, both in their respective proportions;
b) Then, place the analysis plate (8) in the device, by fixing it to the rotating platform (6), in order to avoid any displacement possibility during processing due to the high motor (7) speeds;
c) Close the device by joining the upper part of the device (1) with the lower part (5) and start the device, adjusting the speed according to that recommended for the test;
d) The device activates the camera (3), LEDs (4) and motor (7), according to the following steps:
  i. The motor (7) moves rotationally the platform (6) for a time between 60 and 130 second, during which the reactions takes place;
  ii. The motor (7) stops and the LEDs (4) are turned on;
  iii. The camera (3) captures the image after 2 minutes only, so that weaker reactions are not hidden;
e) LEDs (4) are turned off;
f) The camera's image is sent to the mobile device, which in turn stores this image;
g) The image is treated by image processing techniques;

h) The classification algorithm classifies the occurrence or non-occurrence of agglutination according to the standard deviation value obtained in each of the test containers.

In the event of performing a spinning, proceed as follows:
In a spinning plate place the recommended blood amount in each of the required containers;
Open up the system and place the spinning plate (12) therein, well fixed for preventing any displacement from its place;
Then, close the system, adjust the speed according to the one recommended for the test and press the button to turn on the system and promote shaking;
After spinning, open the system for removing the spinning plate and extracting the plasma;
Finally, discharge the spinning plate in a proper place.

In the case of ABO group and RhD testing 4 containers are used and for RhD phenotype 6 containers are used.

Image Processing Techniques

The image processing techniques to detect the occurrence of agglutination and, therefore, determine the result of the test under analysis comprise the following steps:
a) Extract the green color planes of the captured image by transforming the original 32-bit image into an 8-bit image so it can be used;
b) Separate the blood and reagent mixtures into two regions, designated particle region and background region, by assigning the value 1 (one) to all pixels belonging to a range of established values and assigning the value 0 (zero) to all other pixels in the image that does not belong to such established range;
c) Calculate the threshold value for each pixel based on statistics of the adjacent pixel, using a 32-width and 32-height default matrix (kernel), with a deviation factor which by default is 0.20;
d) In the image, assign the value 1 (one) to existing holes in the particles corresponding to blood and reagent mixtures;
e) Then, remove the particles with the value 1 (one) to remove background noise from the image and ensure that at the end only remain the particles related to test containers;
f) Remove the particles which are on the borders of the image, filling in the position with the same value of the adjacent pixel in order to ensure that only remain for analyzing particles related to test containers;
g) Calculate the metrics on the CenterofMassX and CenterofMassY image, which together provide the coordinates of the center of mass of each particle in the image;
h) Extract the light planes from the original image and transform the image into an 8-bit image, which can now be used by other functions;
i) Reference the object in the image that is an identifying mark of the order in which the test was performed, keeping a profile of such object and searching for such object in each image analyzed by the program, giving the coordinates and calculating the distances to other objects;
j) Identify in each image six containers and present the coordinates of each in order to calculate the aforementioned distances;
k) Quantify a given image region defined by the programmer, using each of the container's coordinates given in the previous function to quantify a set of metrics as average of pixels, minimum value, maximum value, standard deviation and analyzed area, because the standard deviation value determines whether or not agglutination has occurred in each test container.

The image processing techniques have been developed using the Labview software and also with the programming languages C# and C, such that they can be used by different mobile devices. The possibility of having the application in a mobile device enables its worldwide use. The developed software, as mentioned, uses image processing techniques to detect agglutination and classification algorithms to determine the result of the tests performed.

The application's main functions are:
Image Buffer: Store a copy—which allows saving the original image captured by the camera in order to keep it intact for further use later on;
Color Plane Extraction: RGB Green Plane—extracts green planes from the captured image, allowing transforming the original 32-bit image into an 8-bit image, such that it can be used by subsequent functions required for processing;
Auto Threshold Clustering—this function applies a threshold (threshold, in English threshold) based on statistical techniques called clustering and is used to separate the blood and reagent mixtures into two regions, designated "particle region" and "background region". This process consists of changing all pixels belonging to a certain range of established values (designated threshold range) by changing all other pixels in the image to zero (0). It is important to note that the function is automatic and the users need not to specify the range values. To set the threshold, the function automatically uses the histogram values;
Local Threshold: Niblack—in this function the threshold value for each pixel is calculated based on statistics of the adjacent pixel. A 32-width and 32-height default matrix (kernel) is used, with a deviation factor which by default is 0.20. This function is extremely important to isolate particles to be analyzed. After applying this function, particles corresponding to blood and reagent mixtures are then isolated from the rest of the image;
Adv. Morphology: Fill holes—which allow completely filling the existing holes in the particles;
Adv. Morphology: Remove small objects—as the name indicates, it removes small particles, by removing trash background that is spoiling the image and ensuring that ultimately only remain particles relating to test containers;
Adv. Morphology: Remove border objects—removes particles that are on the borders of the image, ensuring once again that remain for analysis particles relating to test containers only;
Particle Analysis—this function is extremely useful since it allows obtaining a series of metrics about the image, such as CenterofMassX and CenterofMassY, which together provide the coordinates of the center of mass of each particle in the image; the center of Mass X is a coordinate that together with the center of Mass Y provide a position in the particle (blood/reagent mixture) which corresponds to the center of mass of such particle—the mass of the particle pixels is averaged and the value obtained according to the following formulae:

$$CenterofmassX = \frac{m_1 x_1 + m_2 x_2 + m_3 x_3 + \ldots + m_n x_n}{m_1 + m_2 + m_3 + \ldots + m_n}$$

$$CenterofmassY = \frac{m_1 y_1 + m_2 y_2 + m_3 y_3 + \ldots + m_n y_n}{m_1 + m_2 + m_3 + \ldots + m_n}$$

Image Buffer: Retrieve Copy—to retrieve the original image saved in the first function presented in such a way that it can be used by the following functions;

Color Plane Extraction: HSL Luminance Plane—extracts light planes from the original image and allows once again transforming the image into an 8-bit image which can now be used by other functions;

Pattern Matching—this function is crucial for determining the test result. Basically, it consists in referencing an object in the image that actually is an identifying mark of the order in which the test was performed. The function save a profile of such object and will try to search for such an object in each of the images that the program analyzes. Once the reference object is found, it returns its coordinates and, based on these, it allows calculating distances to other objects (in this case, to each of the particles corresponding to the test containers). Knowing the distances, these are ordered and the correct order of test analysis obtained, as well as the result of the test performed, which will then be provided by the classification algorithm;

Geometric Matching—this function associated with the previous one help in determining the result of the test. In this case, provided the profile of each test container, the function will identify in each image six containers and will return the coordinates of each container. Through the coordinates of each of them, the aforementioned distances are calculated (from the reference object to each of the containers). In this way, the correct order of the test analysis is known;

Quantify—quantifies a particular image region defined by the programmer, using each of the container's coordinates provided in the previous function. Quantification allows obtaining a set of metrics such as average of pixels, minimum value, maximum value, standard deviation and analyzed area. In this case, the standard deviation value is the important metric for the work, as it is based on this value that it is determined whether or not agglutination has occurred in each test container.

Classification Algorithm—the classification algorithm classifies the occurrence, or not, of agglutination in accordance with the standard deviation value obtained for each of the test containers. If the standard deviation is greater than 16, classifies as agglutinated, if the standard deviation is less than 16 classifies as non-agglutinated. In addition, combination of results according to agglutination and no agglutination allows to identify the test result for each of the tests performed, being either a blood group, an antibody, a compatibility or a disease.

The function that removes border particles eliminates particles that touch the border of the image, that is, the outer boundaries of the image. In other words, if the particle touches the image borders, on the sidelines, it is eliminated. This is used to eliminate the circle made by the system base that is captured by the camera and does—not account for image analysis. No values are used, it is just enough to touch on said image boundaries.

The Image Processing techniques developed and remaining algorithms are capable of being used in mobile devices such as tables and mobile phones with Windows Phone, Android and iOS operating system. These applications are primarily based on capturing an image by the mobile device and processing of such an image by the image processing techniques developed; or image capturing can be performed by the system camera and sent to the mobile device via Bluetooth/Wireless, being the Image Processing of the sent image performed therein by the developed application.

The above described software also allows sending electronic mail and short messages (sms) to a mobile phone with the results of the tests performed, allowing, in the event of tests performed outside the laboratory, to prepare in advance a compatible blood unit.

EXAMPLES

In the following example, results are presented for ABO group and RhD testing, and for RhD phenotyping. Taking into account that occurrence of agglutination identifies the antigen present, in the case of ABO group and RhD testing, there is a range of possible results, some of which are shown in Table 1. Analyzing Table 1, it follows that, for example, Example 1 Agglutinated in the presence of anti-A, anti-AB and anti-D reagents, indicating the presence of antigens A and D. Since D indicates whether it is Rh positive or Rh negative, the occurrence of agglutination indicates positiveness, and therefore the result of this test is A Positive. The same reasoning will be applied to the other examples. For example, Example 4 has 0 Positive as its result, because the single reagent which agglutinated the blood was in the presence of Anti-D reagent, indicating the positiveness of Rh and indicating that no other antigens are present, hence it is a 0 or zero positive.

TABLE 1

Expected results with classification algorithm for ABO group and Rh testing

| | AntiA Reagent | Anti-B Reagent | Anti-AB Reagent | Anti-D Reagent | Result |
|---|---|---|---|---|---|
| Example 1 | Agglutinated | Not Agglutinated | Agglutinated | Agglutinated | A Positive |
| Example 2 | Not Agglutinated | Agglutinated | Agglutinated | Not Agglutinated | B Negative |
| Example 3 | Agglutinated | Agglutinated | Agglutinated | Not Agglutinated | AB Negative |
| Example 4 | Not agglutinated | Not Agglutinated | Not Agglutinated | Agglutinated | O Positive |

In case of RhD phenotype testing, the procedure is similar. The agglutination identifies the presence of the antigen and as such, analyzing one of the examples, e.g. Example 2, taking into account that agglutinated in the presence of anti-D, anti-c, anti-c and anti-E reagents, with no agglutination in the others, the present phenotype is DcCe.

TABLE 2

Results for the phenotype testing with the classification algorithm

| | Anti-D Reagent | Anti-C Reagent | Anti-c Reagent | Anti-E Reagent | Anti-e Reagent | Anti-K Reagent | Result |
|---|---|---|---|---|---|---|---|
| Example 1 | Agglutinated | Not Agglutinated | Agglutinated | Agglutinated | Agglutinated | Not Agglutinated | DcEe |
| Example 2 | Agglutinated | Agglutinated | Agglutinated | Not Agglutinated | Agglutinated | Not Agglutinated | DcCe |

The invention claimed is:

1. A method for detecting immunological agglutination of blood samples using a portable device, the method comprising:
   a) providing a portable device for testing blood samples, the portable device comprising:
      a lower part comprising:
         a rotating platform;
         an analytical plate disposed on the rotating platform, the analysis plate having a plurality of containers; each container adapted to hold a reagent and a sample of blood;
         a motor adapted to cause the rotating platform to rotate; and
         an upper part connected to the lower part, the upper part comprising:
         a peripheral wall having a cylindrical shape;
         a lid;
         a camera disposed at a center of the cylindrical shape, the camera being adapted to capture an image of the plurality of containers of the analysis plate, the camera further being adapted to transmit the image to a processing device configured to use one or more image processing techniques to analyze the image; and
         a plurality of LEDs disposed on the peripheral wall in an arrangement that surrounds the camera, the plurality of LEDs adapted to illuminate the analysis plate;
   b) placing each reagent in a respective containers of the analysis plate, and then a sample of blood to be analyzed, both in respective proportions;
   c) placing the analysis plate in the portable device, fixing the analysis plate to the rotating platform;
   d) closing the device by joining the upper part of the device with the lower part and starting the device;
   e) activating the camera, plurality of LEDs, and motor, according to the following steps:
      i. moving rotationally the platform, via the motor for a time between 60 and 130 seconds, during which the reaction takes place;
      ii. stopping the motor and turning on the plurality of LEDs; and
      iii. after 2 minutes, capturing an image with the camera;
   f) turning off the plurality of LEDs;
   g) sending the camera's image to a processing device, which in turn stores this image;
   h) treating the image by image processing techniques on the processing device, the processing techniques comprising:
      i. extracting green color planes of the captured image by transforming an original 32-bit image into an 8-bit image, so the green color plane can be used;
      ii. separating blood and reagent mixtures into two regions, designated particle region and background region, by assigning a value 1 to all pixels belonging to a range of established values and assigning a value 0 to all other pixels in the image that does not belong to the range of established values;
      iii. calculating a threshold value for each pixel based on statistics of an adjacent pixel, using a 32-width and 32-height default matrix, with a deviation factor which by default is 0.20;
      iv. in the image, assigning a pixel value 1 to existing holes in the particles corresponding to the blood and reagent mixtures;
      v. then, removing particles with the value of 1 pixel to remove background noise from the image and ensure that only particles related to test containers remain;
      vi. removing particles which are the borders of the image, filling in the position with the same value of the adjacent pixel, in order to ensure that only remain for analyzing particles related to containers;
      vii. calculating metrics on a CenterofMassX and CenterofMassY image, which together provide coordinates of a center of mass of each particle in the image;
      viii. extracting light planes from the original image and transform the image into an 8-bit image;
      ix. referencing an object in the image that is an identifying mark of an order in which a test was performed, keeping a profile of the object and searching for the object in each image analyzed, giving coordinates and calculating distances to other objects;
      x. identifying in each image six containers and presenting coordinates of each one in order to calculate the aforementioned distances;
      xi. quantifying a given image region defined by a programmer, using each of the coordinates given in a previous function to quantify a set of metrics as average of pixels, minimum value, maximum value, standard deviation and analyzed area, because the standard deviation value determines whether or not agglutination has occurred in each container; and
   i) classifying an occurrence or non-occurrence of agglutination via a classification algorithm according to a standard deviation value obtained for each of the containers.

2. The method for detecting immunological agglutination of blood samples according to claim 1, wherein a blood to reagent ratio consists of a drop of whole blood having one-fourth of a reagent drop size.

3. The method for detecting immunological agglutination of blood samples according to claim 1, wherein when the standard deviation is higher than 16, the classification algorithm classifies as agglutinated.

4. The method for detecting immunological agglutination of blood samples according to claim 1, wherein when the standard deviation is less than 16, the classification algorithm classifies as not agglutinated.

5. The method for detecting immunological agglutination of blood samples according to claim 1, wherein results of occurrence or non-occurrence of agglutination are sent by SMS or email.

6. The method for detecting immunological agglutination of blood samples according to claim 1, wherein blood type is detected by determining ABO and Rh.